(12) United States Patent
Green et al.

(10) Patent No.: US 9,728,383 B2
(45) Date of Patent: Aug. 8, 2017

(54) METHOD OF CALIBRATING ION SIGNALS

(71) Applicant: Micromass UK Limited, Wilmslow (GB)

(72) Inventors: Martin Raymond Green, Bowdon (GB); Keith Richardson, Derbyshire (GB)

(73) Assignee: Micromass UK Limited, Wilmslow (GB)

( * ) Notice: Subject to any disclaimer, the term of this patent is extended or adjusted under 35 U.S.C. 154(b) by 64 days.

(21) Appl. No.: 14/892,815

(22) PCT Filed: Jun. 9, 2014

(86) PCT No.: PCT/GB2014/051767
§ 371 (c)(1),
(2) Date: Nov. 20, 2015

(87) PCT Pub. No.: WO2014/195734
PCT Pub. Date: Dec. 11, 2014

(65) Prior Publication Data
US 2016/0126074 A1    May 5, 2016

(30) Foreign Application Priority Data

Jun. 7, 2013  (EP) .................................. 13171095
Jun. 7, 2013  (GB) .................................. 1310197.7

(51) Int. Cl.
*H01J 49/04*  (2006.01)
*H01J 49/00*  (2006.01)
*G01N 27/62*  (2006.01)

(52) U.S. Cl.
CPC ........ *H01J 49/0009* (2013.01); *G01N 27/622* (2013.01); *H01J 49/0031* (2013.01)

(58) Field of Classification Search
CPC ... H01J 49/009; H01J 49/0031; G01N 23/622
See application file for complete search history.

(56) References Cited

U.S. PATENT DOCUMENTS

| | | | |
|---|---|---|---|
| 6,649,909 B2 | 11/2003 | Russ et al. | |
| 6,914,240 B2 | 7/2005 | Giles et al. | |
| 6,979,816 B2 | 12/2005 | Tang et al. | |
| 7,034,292 B1 | 4/2006 | Whitehouse et al. | |
| 7,385,190 B2 | 6/2008 | Fischer et al. | |
| 7,728,288 B2 | 6/2010 | Makarov et al. | |
| 7,759,638 B2 | 7/2010 | Makarov | |
| 7,952,070 B2 | 5/2011 | Senko et al. | |
| 8,581,181 B2 | 11/2013 | Giles | |

(Continued)

*Primary Examiner* — Wyatt Stoffa
*Assistant Examiner* — Eliza Osenbaugh-Stewar
(74) *Attorney, Agent, or Firm* — Diederiks & Whitelaw, PLC

(57) ABSTRACT

A method of mass or ion mobility spectrometry is disclosed comprising: providing an ion source for generating analyte ions and reference ions; providing a mass analyzer or ion mobility separator (IMS); providing an ion trap between the ion source and the mass analyzer or IMS; guiding reference ions from the ion source into the ion trap and trapping the reference ions in the ion trap; guiding the analyte ions from the ion source into the mass analyzer or IMS, wherein the analyte ions bypass the ion trap; and releasing reference ions from the ion trap into the mass analyzer or IMS for analysis.

22 Claims, 3 Drawing Sheets

(56) References Cited

U.S. PATENT DOCUMENTS

| | | |
|---|---|---|
| 8,648,293 B2 | 2/2014 | Correale |
| 8,829,430 B2 | 9/2014 | Ledford |
| 2003/0138823 A1 | 7/2003 | Brock et al. |
| 2007/0200060 A1 | 8/2007 | Russ et al. |
| 2007/0205361 A1* | 9/2007 | Russ, IV ............. H01J 49/0009 250/288 |
| 2008/0087814 A1 | 4/2008 | Loucks |
| 2009/0090853 A1* | 4/2009 | Schoen .................. H01J 49/06 250/282 |
| 2012/0049056 A1* | 3/2012 | Zabrouskov ........ H01J 49/0045 250/282 |

* cited by examiner

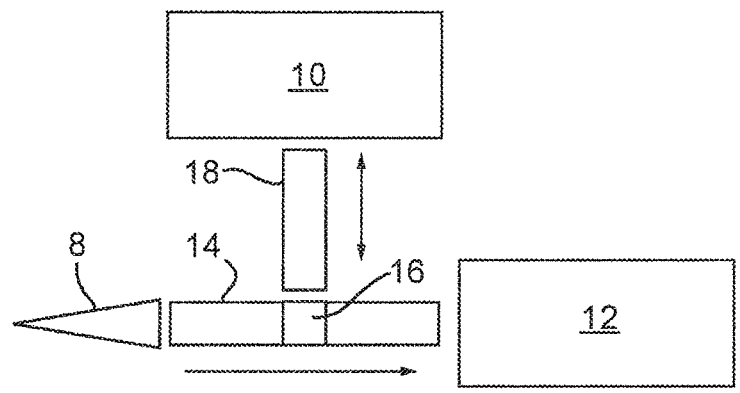
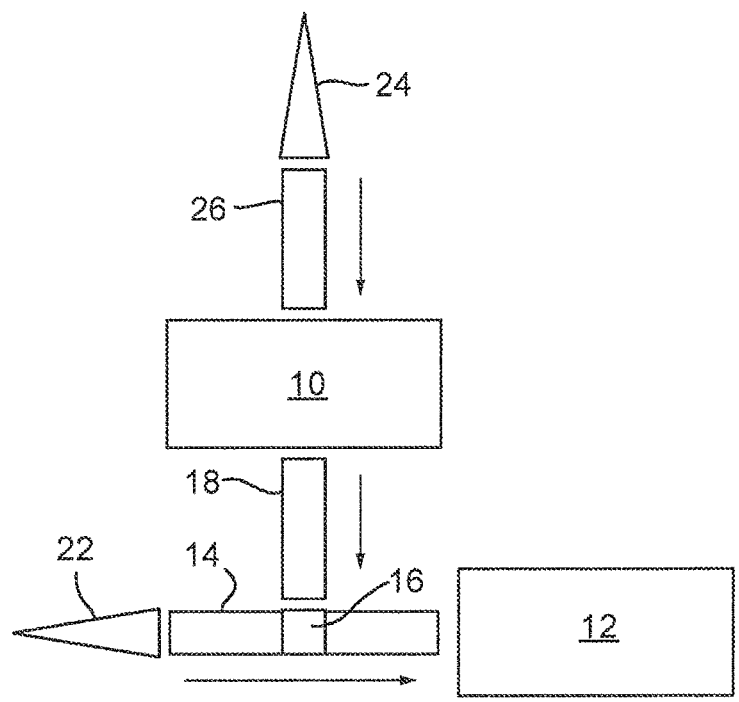

METHOD OF CALIBRATING ION SIGNALS

CROSS-REFERENCE TO RELATED APPLICATION

This application is the National Stage of International Application No. PCT/GB2014/051767, flied 9 Jun. 2014 which claims priority from and the benefit of United Kingdom patent application No. 1310197.7 filed on 7 Jun. 2013 and European patent application No. 13171095.6 filed on 7 Jun. 2013. The entire contents of these applications are incorporated herein by reference.

BACKGROUND OF THE PRESENT INVENTION

The present invention relates to a method of calibrating measurements in a mass spectrometer or ion mobility spectrometer by analysing reference ions.

It is often desired to update the ion mass or mobility calibration during a mass or ion mobility spectrometry experiment or to check other performance characteristics of the instrument. By way of example, temperature fluctuations can affect the mass measurements in a time of flight (TOF) mass spectrometer indirectly through the affect on the power supply and more directly by causing expansion or contraction of the metal in the flight tube. It is desired to calibrate the instrument in order to obtain accurate measurements even in the presence of such fluctuations. A known and extremely effective means of recovering accurate mass measurements in such an arrangement is to use single point lock mass correction. In lock mass corrections, reference ions of known mass are introduced into the mass spectrometer and analysed in order to calibrate the mass measurements. However, conventional implementations of this lock mass acquisition suffer from a variety of drawbacks, as discussed below.

It is possible to use internal or external reference compounds in order to introduce reference ions into the mass spectrometer. Internal reference techniques refer to acquisitions in which a reference compound is measured in arrays that also contain analyte data. In contrast, external reference techniques acquire separate reference data and analyte data arrays.

In internal reference techniques, the reference compound must be present with the analyte. A reference compound may be mixed into the analyte prior to ionisation, or the reference may be a background ion already present in the analyte sample. In either event, the reference compound may compete for the available charge during the ionisation process. This can lead to the signal from the reference ions being suppressed to the point at which the calibration or correction becomes impossible or inaccurate due to ion statistics or interferences. This problem can be circumvented by using an ion source that is separate to the analyte ions source in order to introduce the reference ions into the system. However this inevitably adds complexity and possible points of failure (for example fluidics or pumping requirements) to the instrument. Furthermore, if an analyte has a mass to charge ratio and/or ion mobility that is similar to that of the reference ion, then both the reference ion and analyte ion measurements become compromised.

In external reference techniques, it is usual to interpose acquisition of reference data between analyte data. This often means that analyte data is lost whilst acquiring the reference data. This is obviously undesirable in a quantitative experiment or, for example, when accurate measurement of the position of a chromatographic peak is required. The use of an external reference also requires a mechanism capable of switching the acquisition between analyte and reference modes. This may introduce mechanical complexity or the need for a secondary ion source in order to ionise the reference compound.

It is therefore desired to provide an improved method of mass spectrometry and an improved mass spectrometer.

SUMMARY OF THE PRESENT INVENTION

From a first aspect, the present invention provides a method of mass or ion mobility spectrometry comprising:
providing an ion source for generating analyte ions and an ion source for generating reference ions;
providing an analyser;
providing an ion trap between the ion source for generating reference ions and the analyser;
directing reference ions from the ion source for generating reference ions into the ion trap and trapping the reference ions therein;
directing analyte ions from the ion source for generating analyte ions into the analyser without the analyte ions passing into the ion trap, and analysing the analyte ions in the analyser; and
releasing reference ions from the ion trap into the analyser and analysing the reference ions, wherein the trapped reference ions are controllably released from the ion trap such that only a portion of the reference ions trapped in the ion trap are released at any given time.

The use of an ion trap to trap and release reference ions in the present invention enables the supply of reference ions to be stable and more reliable, as compared to the use of a reference ion source to supply reference ions directly to the analyser. Furthermore, by controllably releasing the reference ions from an ion trap it is ensured that reference ions are released to the analyser at a rate that provides adequate sensitivity whilst avoiding saturation of the analyser's detector.

It has been recognised in the present invention that it is particularly important to carefully control the amount of reference ions being delivered to the analyser so as to ensure adequate sensitivity but also avoid saturating the detection system of the analyser. US 2010/0176295 discloses a mass spectrometer having a Y-shaped ion guide for transmitting ions from two different ion sources to an analyser. One of the ion sources may be used for ion calibration. However, the spectrometer does not trap calibrant/reference ions in an ion trap, whilst causing the analyte ions to bypass such an ion trap.

Furthermore, calibrant/reference ions are not controllably released from such an ion trap into the analyser such that only a portion of the reference ions trapped in the ion trap are released at any given time. As such, the spectrometer of US 2010/0176295 is unable to adequately control the rate at which calibrant/reference ions are transmitted into the analyser so as to provide adequate sensitivity whilst avoiding saturation of the detection system.

The present invention also enables reference ions and analyte ions to be analysed whilst using only a single ion source at any given time.

The ion trap is also able to be easily positioned near to the analyser so that the reference ions can pass to the analyser quickly and without having to pass through the ion manipulation devices that the analyte ions pass through on the way to the analyser. Accordingly, the ion trap is preferably provided adjacent to the analyser. The spectrometer may comprises ion manipulation devices that the analyte ions are transmitted through between the analyte ion source and the analyser, whereas the reference ions can be released from the ion trap into the analyser without being transmitted through these ion manipulation devices.

The analyser is preferably a mass analyser or an ion mobility separator (IMS). The analyser may comprise an ion detector.

Preferably, the reference ions and analyte ions are analysed by the analyser to provide mass to charge ratio measurements or ion mobility measurements, wherein the mass to charge ratio or ion mobility of the reference ions is known or previously determined prior to the analysis of the reference ions in the analyser, and wherein the mass to charge ratio measurements or ion mobility measurements of the analyte ions are adjusted or calibrated based on the difference between the known or previously determined mass to charge ratio or mobility and the measured mass to charge ratio or mobility of the reference ions.

Alternatively, or additionally, the reference ions may be analysed by the analyser to provide mass to charge ratio measurements or ion mobility measurements, wherein the mass to charge ratio or ion mobility of the reference ions is known or previously determined prior to the analysis of the reference ions in the analyser, and wherein the operation of the mass or ion mobility spectrometer is controlled or adjusted based on the difference between the known or previously determined mass to charge ratio or mobility and the measured mass to charge ratio or mobility of the reference ions so as to maintain a predetermined operational characteristic of the mass or ion mobility spectrometer at a desired level, e.g. to maintain the mass or ion mobility spectrometer at a desired resolution or sensitivity.

The reference ions and analyte ions may be guided through the same first ion guide, wherein the reference ions are directed from the ion guide into the trap and trapped therein, and wherein the analyte ions are directed from the ion guide into the analyser for analysis, the analyte ions having bypassed the ion trap.

The analyte ions and reference ions are preferably guided along an axis through the ion guide, and an electric field is preferably applied to the reference ions whilst they are within the ion guide or at the exit of the ion guide such that the reference ions are diverted off the axis and transmitted downstream into the ion trap and trapped therein. Alternatively, or additionally, an electric field may be applied to the analyte ions whilst they are within the ion guide or at the exit of the ion guide such that the analyte ions are diverted off the axis and transmitted downstream into the analyser whilst bypassing the ion trap.

The reference ions may be ejected or directed from the first ion guide directly into the ion trap. Alternatively, the reference ions may be ejected or directed from the first ion guide into a further ion guide that guides the reference ions into the ion trap.

The analyte ions and reference ions may be provided to the ion guide in a spatially separated manner or may be spatially separated within the ion guide. The electric field may then cause the analyte ions and reference ions to proceed along different pathways.

The analyte and reference ions are preferably supplied to the first ion guide in a manner such that when analyte ions are received in the ion guide reference ions are not received, and when reference ions are received in the ion guide analyte ions are not received. This may be achieved by arranging a mass filter upstream of the first ion guide so as to selectively transmit either analyte ions or reference ions to the first ion guide. Alternatively, reference ions and analyte ions may be generated alternately by a single ion source or by multiple ion sources.

A second ion guide may be provided between the first ion guide and the analyser for guiding ions to the analyser, wherein analyte ions are transmitted from the first ion guide into the second ion guide and then into the analyser whilst bypassing the ion trap, and wherein reference ions are transmitted from the ion trap into the second ion guide and into the analyser.

The first and second ion guides preferably have longitudinal axes along which ions travel as they pass through the ion guides, and wherein the longitudinal axes are preferably coaxial and arranged such that ions which exit the first ion guide along its longitudinal axis are directed into the second ion guide.

The ion trap may have a longitudinal axis and ions may be radially confined on said axis, wherein the axis is substantially parallel to and displaced from said longitudinal axes of the first and second ion guides.

The analyte ions and reference ions may be generated by the same ion source.

The analyte ions and reference ions may be generated simultaneously by using an internal reference compound. The resulting analyte ions and reference ions may be separated from each other such that the reference ions are subsequently directed to the ion trap and the analyte ions bypass the ion trap. Alternatively, the analyte ions and reference ions may be generated by the same ion source sequentially using an external reference compound.

Alternatively, the analyte ions may be generated by a first ion source and the reference ions may be generated by a second, different ion source. The analyte ions are preferably guided from the analyte ion source into the analyser by a first ion guide and the reference ions are preferably guided from the reference ion source into the ion trap by a second, different ion guide.

The analyte and reference ions may be generated simultaneously or sequentially.

In the arrangement wherein the source of reference ions is separate from the analyte ion source it is possible for the ion trap to be filled continuously during the experiment, so that the ion trap acts as a reservoir for reference ions. This is particularly advantageous when the source of reference ions is weak or variable, in which case the ion trap allows regulated amounts of reference ions to be delivered on demand and more rapidly than would otherwise be possible.

Preferably, the reference ions are released from said ion trap into said first ion guide and are then guided into the analyser. The first ion guide may comprise a switching device that operates in a first mode to allow analyte ions to pass from the analyte ion source into the analyser, and that operates in a second mode to prevent analyte ions from passing from the analyte ion source to the analyser and to allow reference ions to pass from the ion trap to the analyser.

Alternatively, the reference ions may be released from the ion guide directly into the analyser or into a third, different ion guide that guides the reference ions into the analyser.

A mass analyser and/or ion mobility separator and/or ion filter may be provided between the source of analyte ions and the first ion guide for mass analysing analyte ions, separating analyte ions according to their mass to charge ratios or ion mobilities, or mass selectively transmitting analyte ions. Alternatively, or additionally, a mass analyser and/or ion mobility separator and/or ion filter may be provided between the source of reference ions and the first ion guide for mass analysing reference ions, separating reference ions from other ions according to their mass to charge ratios or ion mobilities, or mass selectively transmitting reference ions.

The ion filter between the source of analyte ions or reference ions and the first ion guide may be a FAIMS device.

An ion filter may be provided between the source of reference ions and the ion trap so as to allow full utilisation of the space-charge capacity of the ion trap and/or to prevent unwanted reactions within the ion trap.

Preferably, the analyte ions are supplied to the analyser and analysed therein after the reference ions have been trapped in the ion trap.

The reference ions may be released from the ion trap and analysed by the analyser whilst the analyte ions are being analysed or after the analyte ions have been analysed by the analyser. Analyte ions may be prevented from entering the analyser whilst reference ions are released from the ion trap into the analyser.

The method may comprise operating a first mode in which analyte ions are analysed in the analyser and reference ions are not, operating a second mode in which reference ions from the ion trap are analysed in the analyser and analyte ions are not, and repeatedly alternated between these first and second modes.

Analyte ions may be trapped during the second mode and may later be released for analysis in the analyser when the first mode is subsequently operated.

The first ion guide may be operated so as to prevent analyte ions from passing into the analyser during said second mode. The first ion guide may trap analyte ions therein during this period or may divert the analyte ions into an analyte ion trap, e.g. to be stored and then analysed in the analyser after the reference ions have been analysed.

Preferably, only a portion of the reference ions within the ion trap are released to the analyser at any given time.

A plurality of ion packets may be released from the ion trap before the ion trap is refilled with reference ions from the reference ion source. When the method is operated in said first and second modes described above, the method may be operated in the second mode a plurality of times before refilling the ion trap with reference ions.

The analyser may discontinuously analyse ions in a plurality of analysis cycles, wherein reference ions are guided into the analyser as a series of ion packets that are synchronised with the analysis cycles such that an ion packet is analysed in at least one cycle or between cycles; and wherein spectral data from the reference ions analysed in separate analysis cycles is combined to produce combined reference ion data or a combined reference ion peak that is used to either:

(i) adjust or calibrate the mass or mobility measurements of the analyte ions; or (ii) maintain a predetermined operational characteristic of the mass or ion mobility spectrometer at a desired level, e.g. to maintain the mass or ion mobility spectrometer at a desired resolution or sensitivity.

Preferably, the analyte ions do not pass into the ion trap and/or the only ions that enter the ion trap are the reference ions. This prevents undesired ion-ion reactions in the ion trap, avoids space-charge problems in the ion trap, and avoids interferences in the spectra of the analysed ions.

Preferably, the reference ions are released from the ion trap into the analyser for calibrating the analyser for the analysis of the analyte ions that have bypassed the ion trap.

Preferably, the analyte ions are transmitted from the ion source of analyte ions to the analyser without being reacted with other ions or molecules, and/or without being fragmented.

The reference ions may be released from the ion trap at a substantially constant charge per second. Alternatively, the reference ions may be discontinuously released from the ion trap in ion packets having substantially the same charge.

Preferably, the reference ions are released from the ion trap at a rate such that the reference ions do not saturate the analyser or a detector of said analyser.

The analyser may analyse said reference ions and analyte ions simultaneously, or may analyse said reference ions and analyte ions separately.

The analyser may be a time of flight mass analyser, and is preferably an orthogonal acceleration TOF mass analyser.

Reference ions may be continually released from the ion trap and transmitted to the analyser. The ions may be released from the ion trap at a substantially constant charge per second. Alternatively, reference ions may be released from the ion trap discontinuously as a series of ion packets. The ion packets may contain substantially the same amount of charge. This pulsed beam of reference ions may be converted into a pseudo-continuous or substantially continuous beam by collisions between the reference ions and a buffer gas arranged between the ion trap and analyser. For example, the buffer gas may be arranged in an ion guide such as an RF ion guide.

A DC potential barrier or an RF pseudo-potential barrier may be arranged at the exit of the ion trap to prevent reference ions from exiting the ion trap and passing to the analyser. Ions may be released from the ion trap into the analyser by lowering the potential of the barrier or by removing the barrier. Alternatively, the DC barrier or RF pseudo-potential barrier may remain constant and an electric field may be used to drive the reference ions over the potential barrier when it is desired to eject reference ions from the ion trap and into the analyser.

The mass spectrometer may comprise means for controlling the rate at which reference ions that have been released from the ion trap are received at the analyser. This may be useful in situations where it is not possible to control precisely the number of ions released from the ion trap. Ions may be released from the ion trap at a relatively high rate and a downstream mechanism may be used to control the ion delivery so that the reference ions are received at the analyser at a relatively low rate. For example, the ion trap may eject reference ions into a second ion trap at a first rate and the second ion trap may release the reference ions at a lower rate.

A dual ion trap arrangement may be provided comprising a high charge capacity reservoir for reference ions and a low charge capacity trapping region for reference ions arranged downstream thereof. The low charge capacity trapping region may be filled with reference ions from the reservoir and reference ions may then be released from the low charge capacity trapping region into the analyser in a controlled manner. Reference ions may be transferred from the reservoir to the low charge capacity trapping region during periods in which the analyser is analysing the analyte ions.

The two ion traps may be two separate ion trapping devices or may be two or more regions separated by DC or RF pseudo-potential barriers. For example, two trapping regions could be provided within an ion guide by applying DC or RF potentials to the ion guide so as to create the barriers between the trapping regions. Reference ions may be ejected from a main trapping region to another trapping region within the ion guide. The potential barrier(s) forming said another trapping region may then be conveyed along the ion guide so as to drive the reference ions in that trapping region towards the exit of the ion guide and into the analyser.

A dual ion trap arrangement may be provided to allow storage of more than one type of reference ion where these ions might otherwise react with each other. In particular the ion traps may contain positively and negatively charged ions respectively. More than two ion traps could be employed for the same purpose, or simply to provide more capacity.

The method may comprise filtering ions in an ion filter, separating ions in a separator or fragmenting ions in a fragmentation device prior to analysis in the analyser; wherein the ion trap is arranged such that the reference ions are guided from the ion trap to the analyser without passing through the ion filter, ion separator or fragmentation device.

The ion trap is preferably arranged in a vacuum chamber.

The ion source(s) is preferably arranged in a vacuum chamber, rather than being substantially at atmospheric pressure.

A mixture of ions may be produced by the ion source that generates the reference ions and this mixture of ions may become trapped within the ion trap. However, it may be desirable that only reference ions of a particular mass to charge ratio or range of mass to charge ratios are desired to be analysed by the analyser. Accordingly, the spectrometer may mass selectively eject ions of a particular mass to charge ratio or range of mass to charge ratios from the ion trap and into the analyser. Additionally, or alternatively, voltages may be applied to the ion trap to eject and discard ions which are not desired to be used as reference ions and which are not desired to enter the analyser. For example, a broadband resonance voltage may be applied to the ion trap in order to eject unwanted ions. Alternatively, or additionally, a filter (including but not limited to a mass to charge ratio filter, an ion mobility filter or a FAIMS filter) may be arranged upstream of the ion trap and used to select the ions that are transmitted from the source of reference ions to the ion trap. Ions which are not desired to be used as reference ions can therefore be prevented from entering the ion trap and prevented from entering the analyser with the desired reference ions. Alternatively, or additionally, a mass filter may be arranged downstream of the ion trap and used to select the ions that are transmitted from the ion trap to the analyser. Ions which are not desired to be used as reference ions can therefore be prevented from entering the analyser with the desired reference ions.

Two or more ion traps may be provided for trapping the reference ions and the reference ions may be directed into the two or more ion traps and trapped therein. The reference ions may then be released from the two or more ion traps into the analyser. The two or more ion traps may be used, for example, in order to increase the charge capacity of the trapped reference ions. Alternatively, or additionally, different reference ions may be stored in different ones of the ion traps. For example, reference ions of different polarities may be stored in different ion traps, or reference ions that would otherwise react with each er may be stored in different ion traps.

The method of mass or ion mobility spectrometry is performed on a mass or ion mobility spectrometer. The reference ions are analysed by the analyser and the resulting reference ion signal may be used to check a performance characteristic of the spectrometer. For example, the performance characteristic may be one of the following: sensitivity of the spectrometer; mass to charge ratio resolution and/or peak shape; or ion mobility resolution and/or peak shape.

The reference ions are analysed by the analyser and the resulting reference ion signal may be used to update one or more operational parameter of the spectrometer. For example, the operational parameter may be one of the following: the gain of a detector in the spectrometer; one or more voltages applied to ion optical elements within the spectrometer; an event timing or delay period in the method of spectrometry.

It is contemplated that the trapped reference ions need not be controllably released from the ion trap such that only a portion of the reference ions trapped in the ion trap are released at any given time.

Accordingly, from a second aspect the present invention provides a method of mass or ion mobility spectrometry comprising:

providing an ion source for generating analyte ions and an ion source for generating reference ions;

providing an analyser;

providing an ion trap between the ion source for generating reference ions and the analyser;

directing reference ions from the ion source for generating reference ions into the ion trap and trapping the reference ions therein;

directing analyte ions from the ion source for generating analyte ions into the analyser without the analyte ions passing into the ion trap, and analysing the analyte ions in the analyser; and releasing reference ions from the ion trap into the analyser and analysing the reference ions.

The reference ions and analyte ions are preferably guided through the same first ion guide, wherein the reference ions are directed from the ion guide into the trap and trapped therein, and wherein the analyte ions are directed from the ion guide into the analyser for analysis, the analyte ions having bypassed the ion trap.

The method according to the second aspect of the invention may have any one or combination of the optional or preferred features described in relation to the first aspect of the present invention.

The present invention also provides a spectrometer arranged and configured to perform any one or any combination of any two or more of the methods described herein above.

Accordingly, the present invention provides a mass or ion mobility spectrometer comprising:

an ion source for generating analyte ions and an ion source for generating reference ions;

an analyser;

an ion trap arranged between the ion source for generating reference ions and the analyser; and control means arranged and configured to:

direct reference ions from the ion source for generating reference ions into the ion trap and trap the reference ions therein;

direct analyte ions from the ion source for generating analyte ions into the analyser without the analyte ions passing into the ion trap, and to analyse the analyte ions in the analyser; and release the reference ions from the ion trap into the analyser so as to analyse the reference ions, preferably wherein the trapped reference ions are controllably released from the ion trap such that only a portion of the reference ions trapped in the ion trap are released at any given time.

The mass spectrometer may comprise:

(a) an ion source selected from the group consisting of: (i) an Electrospray ionisation ("ESI") ion source; (ii) an Atmospheric Pressure Photo Ionisation ("APPI") ion source; (iii)

an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source: (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may comprise an electrostatic ion trap or mass analyser that employs inductive detection and time domain signal processing that converts time domain signals to mass to charge ratio domain signals or spectra. Said signal processing may include, but is not limited to, Fourier Transform, probabilistic analysis, filter diagonalisation, forward fitting or least squares fitting.

The mass spectrometer may either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may comprise a device arranged and adapted to supply an AC or RF voltage to the electrodes. The AC or RF voltage preferably has an amplitude selected from the group consisting of: (i)<50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii)

350-400 V peak to peak; (ix) 400-450 V peak to peak; (x) 450-500 V peak to peak; and (xi) >500 V peak to peak.

The AC or RF voltage preferably has a frequency selected from the group consisting of: (i)<100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i)<0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

In order to effect Electron Transfer Dissociation, optionally: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xi) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene reagent ions.

The preferred embodiment of the present invention provides a means of delivering controlled quantities of reference ions to a mass analyser or IMS during a spectral acquisition period. As the ion trap is filled with reference ions and the reference ions are released from the ion trap, rather than switching the ion source between analyte ions and reference ion generation modes, the method does not require any interruption to the analyte ionisation process or the movement of any parts in the ion source. The method therefore improves the ion source with robustness and reduces maintenance time. Also, the ion trap may be arranged within the spectrometer and configured to supply ions to the mass analyser or IMS at a high speed. The analyte duty cycle can therefore be improved, thereby effectively improving sensitivity and quantitative fidelity of the spectrometer.

BRIEF DESCRIPTION OF THE DRAWINGS

Various embodiments of the present invention will now be described, by way of example only, and with reference to the drawings, in which:

FIG. 4 shows an alternative embodiment of the present invention wherein ions are switched between an ion trap and an ion analyser;

FIG. 5 shows an alternative embodiment that is similar to that of FIG. 4 except that it comprises separate analyte ion reference ion sources.

DETAILED DESCRIPTION OF EMBODIMENTS

Figure 1:
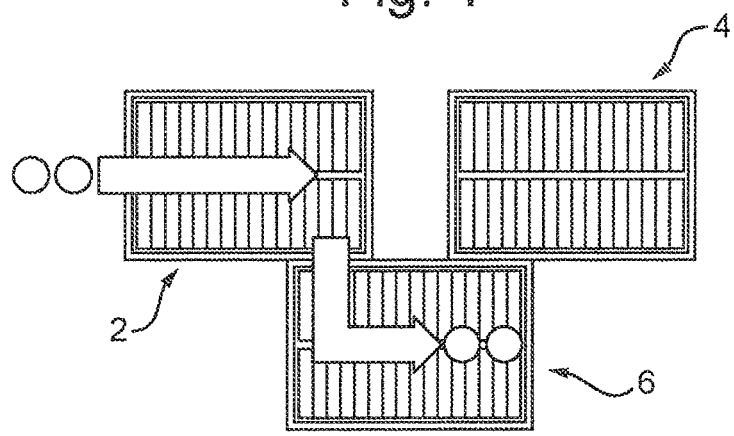
FIG. 1 shows a schematic of a preferred embodiment of the present invention, operating in a mode wherein reference ions are diverted into an ion trap.

FIG. 1 shows a preferred embodiment of the present invention comprising an entrance ion guide 2, an ion trap 6 and an exit ion guide 4. The entrance ion guide 2, ion trap 6 and exit ion guide 4 are formed from electrodes and voltages are applied to the electrodes so as to radially confine ions therein. Each of the entrance ion guide 2 and the exit ion guide 4 radially confines ions therein along an axis and the axes of the two ion guides 2,4 are coaxial. The ion trap 6 radially confines ions therein along an axis, that is parallel to and spaced apart from the axes through the entrance and exit ion guides 2,4.

In a first mode of operation reference ions are generated upstream of the entrance ion guide 2 and these ions are received in the entrance ion guide 2. The reference ions are guided through the entrance ion guide 2 and are then radially ejected into the ion trap 6. The reference ions then remain trapped within the ion trap 6 for subsequent use.

Figure 2:
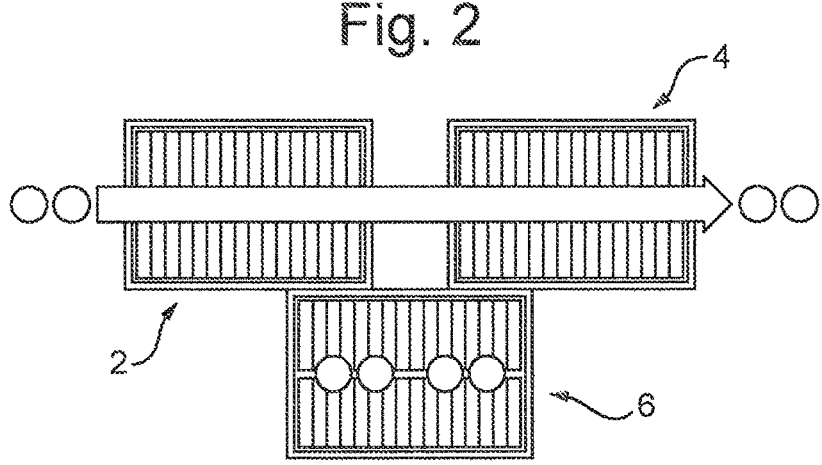
FIG. 2 shows the embodiment of FIG. 1, operating in a mode wherein analyte ions bypass the ion trap.

FIG. 2 shows a schematic of a second mode of operation, at a point after the reference ions have been trapped in the ion trap 6. In this mode of operation, the reference ions are not supplied to the entrance ion guide 2 and analyte ions are supplied to the entrance ion guide 2 instead. The analyte ions are guided through the entrance ion guide 2 and into the exit ion guide 4. The ions are then guided through the exit ion guide 4 and to a mass analyser or ion mobility separator that is arranged downstream (not shown). It is contemplated that the exit ion guide 4 may form at least a part of the ion mobility separator. This mode of operation enables the analyte ions to bypass the ion trap 6 and to be mass analysed and/or analysed by ion mobility separation.

Figure 3:
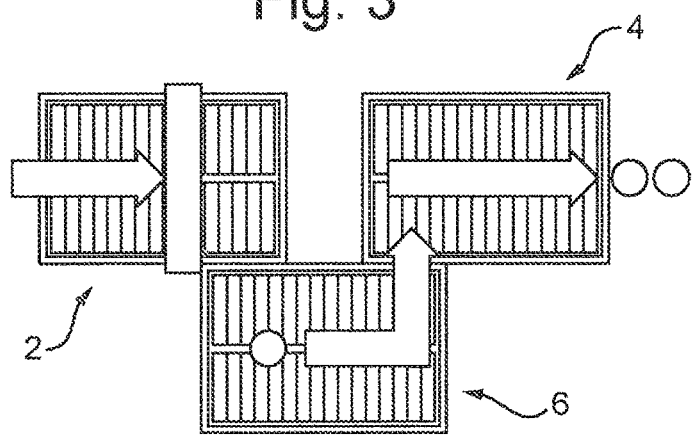
FIG. 3 shows the embodiment of FIG. 1, operating in a mode wherein reference ions from the ion trap are being analysed.

FIG. 3 shows a schematic or a third mode of operation that may be performed subsequent to the second mode of operation described above in relation to FIG. 2. According to the third mode of operation, the entrance ion guide 2 is operated so as to prevent analyte ions from passing into the exit ion guide 4. The analyte ions may be trapped within the entrance ion guide or may be directed into an analyte ion trap (not shown). At least some of the reference ions within the reference ion trap 6 are then ejected from the ion trap 6 into the exit ion guide 4. These reference ions are then guided downstream to the mass analyser or ion mobility separator and analysed. As the analysed properties of the reference ions are known, the analysis of the reference ions enables the calibration of the mass analyser or ion mobility separator. After the reference ions have been analysed the mode of operation described in relation to FIG. 2 is reverted to and analyte ions are analysed again. If analyte ions were trapped during the period in which the reference ions were analysed, rather than simply being discarded, then these analyte ions may then be analysed. Alternatively, analyte ions that are newly received in the ion guide 2 may be analysed. The method may repeatedly alternate between the modes described in relation to FIGS. 2 and 3 so as to alternately analyse analyte ions and reference ions.

FIG. 4 shows another embodiment comprising a source of reference ions and analyte ions 8, an ion trap 10 and an analyser 12. The source of reference ions and analyte ions 8 may be a single ion source or may comprise a reference ion source and a separate analyte ion source. The analyser 12 may be a mass analyser or an ion mobility separator (IMS).

A first ion guide 14 is arranged between the ion source 8 and the analyser 12. A switching mechanism 16 is provided in the first ion guide 14 and a second ion guide 18 extends from the switching mechanism 16 to the ion trap 10. The switching mechanism 16 is configured to divert ions between the analyser 12 and the ion trap 10, as will be described further below. The switching device 16 comprises one or more electrodes for diverting the ions.

In a first mode of operation, reference ions from the ion source 8 pass into the first ion guide 14 and are diverted into the second ion guide 18 by the switching mechanism 16. The reference ions are guided through the second ion guide 18 into the ion trap 10. The reference ions then remain trapped within the ion trap 10 for subsequent use.

In a second mode of operation, at a point after the reference ions have been trapped in the ion trap 10, analyte ions are supplied to the first ion guide 14. The analyte ions are guided through the first ion guide 14 and into the analyser 12. The switching device 16 does not direct the analyte ions into the ion trap 10. This mode of operation enables the analyte ions to bypass the ion trap 10 and be analysed by the analyser 12.

In a third mode of operation that may be performed subsequent to the second mode of operation described above, analyte ions are prevented from passing to the mass analyser 12. This may be performed by the switching device 16 arranging a blocking potential in the first ion guide 14. Analyte ions may be trapped within the entrance end of the first ion guide 14 or may be directed into an analyte ion trap (not shown). At least some of the reference ions within the reference ion trap 10 are then ejected from the ion trap 10 into the second ion guide 18. These reference ions are then guided into the first ion guide 14 and are directed by the switching mechanism 16 to pass into the analyser 12 for analysis. As the analysed properties of the reference ions are known, the analysis of the reference ions enables the calibration of the analyser 12. After the reference ions have been analysed the second mode of operation may be reverted to and the analyte ions may be analysed again. If analyte ions were trapped during the period in which the reference ions were analysed, rather than simply being discarded, then these analyte ions may then be analysed. Alternatively, analyte ions that are newly received in the first ion guide 14 may be analysed. The method may repeatedly alternate between the second and third modes so as to alternately analyse analyte ions and reference ions.

FIG. 5 shows and embodiment that is similar to FIG. 4 and wherein like elements have like reference numbers. However, in the embodiment of FIG. 5 the reference ions and the analyte ions do not both enter the entrance end of the first ion guide 14. Rather, an analyte ion source 22 is arranged at the entrance end of the first ion guide 14 and a separate reference ion source 24 is provided that is interfaced with the ion trap 10 by a third ion guide 26.

In a first mode of operation, reference ions from the reference ion source 24 pass into the third ion guide 26 and are guided through the third ion guide 26 into the ion trap 10. The reference ions then remain trapped within the ion trap 10 for subsequent use.

In a second mode of operation, analyte ions are supplied to the first ion guide 14. The analyte ions are guided through the first ion guide 14 and into the analyser 12. The first and second modes may be operated concurrently or sequentially.

In a third mode of operation that may be performed concurrently or subsequent to the second mode of operation, at least some of the reference ions are ejected from the ion trap 10 into the second ion guide 18. These reference ions are then guided into the first ion guide 14 and are directed by the switching mechanism 16 to pass into the analyser 12 for analysis. As the analysed properties of the reference ions are known, the analysis of the reference ions enables the calibration of the analyser 12. If the second and third modes are performed sequentially, rather than concurrently, then after the reference ions have been analysed the second mode of operation may be reverted to and the analyte ions may be analysed again.

Analyte ions may be prevented from passing to the mass analyser 12 during the third mode. This may be performed by the switching device 16 arranging a blocking potential in the first ion guide 14. Analyte ions may be trapped within the entrance end of the first ion guide 14 or may be directed into an analyte ion trap (not shown).

Figure 6:
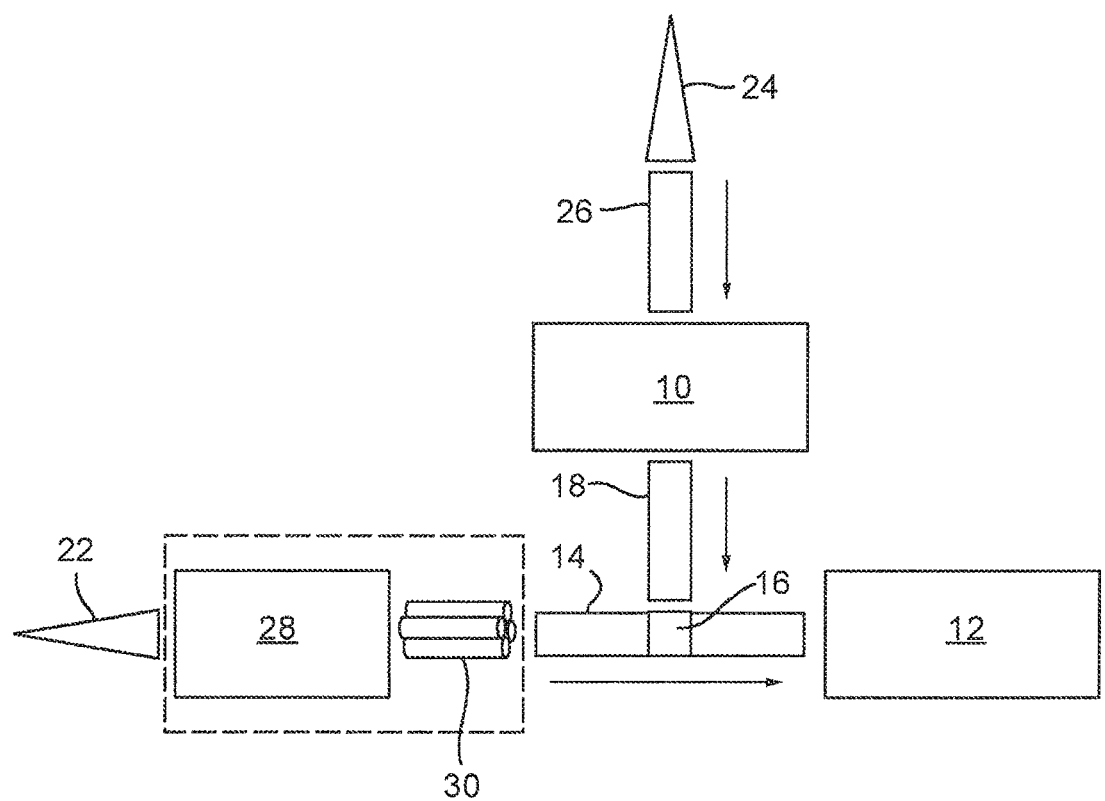
FIG. 6 shows a further embodiment of the present invention that is similar to that of FIG. 5, except that additional devices are arranged between one of the ion sources and the ion analyser.

FIG. 6 shows an embodiment that is similar to FIG. 5 and wherein like elements have like reference numbers. However, in the embodiment of FIG. 6 an ion mobility separator 28 and a quadrupole mass filter 30 are arranged between the source of analyte ions 22 and the first ion guide 14. The ion mobility separator 28 separates the analyte ions according to their ion mobility as they pass through the ion mobility separator 28. The quadrupole 30 may mass selectively transmit analyte ions to the first ion guide 14. The mass to charge ratios of the ions transmitted may vary with time. The analyser 12 in this embodiment is preferably a mass analyser.

It is preferred that the ion trap 10 is filled with reference ions before the start of an experiment. It is also preferred that only some of the reference ions are released from the ion trap 10 during any release cycle such that analyte ion and reference ion analysis cycles can be repeatedly performed without having to refill the ion trap with reference ions.

During the experiment, reference ions can be rapidly delivered to the mass analyser 12 or ion mobility separator 12 and in controlled amounts as required. This allows reference ion spectra to be acquired between analyte ion spectra substantially without discarding analyte ions. This leads to a high duty cycle technique that avoids errors in quantitation due to missing analyte data. By way of example, if a peak comprising 1000 reference ions is required in order to make a statistically accurate reference measurement and a reference measurement is required every 30 seconds, then a trap with a capacity of $10^6$ ions would provide enough reference ions for an acquisition period of over 8 hours.

In order to avoid detector saturation, it may be necessary to spread the packet of reference ions released from the ion trap 10 so that reference ions are delivered to the detector 12 over a time period. For example, in an orthogonal acceleration TOF experiment the reference ion packet may need to be spread over multiple pushes of the extraction region, leading to a consequent loss of analyte duty cycle. This problem can be mitigated in the preferred embodiment by arranging for more frequent acquisitions of packets of reference ions containing fewer ions. Multiple reference spectra may then be combined to produce a reference peak containing a sufficient number of reference ions to generate the required statistical precision.

Although the present invention has been described with reference to preferred embodiments, it will be understood by those skilled in the art that various changes in form and detail may be made without departing from the scope of the invention as set forth in the accompanying claims.

For example, the source of reference ions 24 may be the same ion source as is subsequently used for generating the analyte ions. Alternatively, a conventional lock mass source may be used for generating the reference ions.

One possible implementation of the ion trap 10 is shown in the figures. Each of the ion trap 10 and ion guides 3,4,14,18,26 may be constructed from a plurality of electrodes that are aligned to form ion guiding paths. A portion of the entrance ion guide is parallel and adjacent to a portion of the ion trap 10. The electrodes of the entrance ion guide 2 and ion trap 10 are configured, and voltages are applied to these electrodes, such that reference ions are radially ejected from the entrance ion guide 2 into the ion trap 10 and are then radially confined within the ion trap 10. Similarly, a portion of the exit ion guide 4 is parallel and adjacent to a portion of the ion trap 10. The electrodes of the exit ion guide 4 and ion trap 10 are configured, and voltages are applied to these electrodes, such that reference ions are radially ejected from the ion trap 10 into the exit ion guide 4 and are then radially confined within the exit ion guide 4. The ion trap 10 may be conjoined with the entrance and exit ion guides 2,4 to perform the above functions by being constructed as described in US 2011/0049357. However, it is also contemplated that other configurations of ion traps and ion guides could be used according to the present invention. It is desirable that it should be possible to extract controlled numbers of ions from the ion trap while the total charge within the trap becomes depleted.

One or more ion species may be used as the reference ions, thus allowing single or multi-point reference correction. During selection of the reference compounds consideration should be given as to the stability of the reference ions within the ion trap, e.g. to avoid unwanted ion-ion reactions or fragmentation.

The invention claimed is:

1. A method of mass or ion mobility spectrometry comprising:
   providing an ion source for generating analyte ions and an ion source for generating reference ions;
   providing an analyser;
   providing an ion trap between the ion source for generating reference ions and the analyser;
   directing reference ions from the ion source for generating reference ions into the ion trap and trapping the reference ions therein;
   directing analyte ions from the ion source for generating analyte ions into the analyser without the analyte ions passing into the ion trap, and analysing the analyte ions in the analyser; and
   releasing reference ions from the ion trap into the analyser and analysing the reference ions, wherein the trapped reference ions are controllably released from the ion trap such that only a portion of the reference ions trapped in the ion trap are released at any given time.

2. The method of claim 1, wherein the reference ions and analyte ions are analysed by the analyser to provide mass to charge ratio measurements or ion mobility measurements, wherein the mass to charge ratio or ion mobility of the reference ions is known or previously determined prior to the analysis of the reference ions in the analyser, and wherein the mass to charge ratio measurements or ion mobility measurements of the analyte ions are adjusted or calibrated based on the difference between the known or previously determined mass to charge ratio or mobility and the measured mass to charge ratio or mobility of the reference ions.

3. The method of claim 1, wherein the reference ions are analysed by the analyser to provide mass to charge ratio measurements or ion mobility measurements, wherein the mass to charge ratio or ion mobility of the reference ions is known or previously determined prior to the analysis of the reference ions in the analyser, and wherein the operation of the mass or ion mobility spectrometer is controlled or adjusted based on the difference between the known or previously determined mass to charge ratio or mobility and the measured mass to charge ratio or mobility of the reference ions so as to maintain a predetermined operational characteristic of the mass or ion mobility spectrometer at a desired level, e.g. to maintain the mass or ion mobility spectrometer at a desired resolution or sensitivity.

4. The method of claim 1, wherein reference ions and analyte ions are guided through the same first ion guide, wherein the reference ions are directed from the ion guide into the trap and trapped therein, and wherein the analyte ions are directed from the ion guide into the analyser for analysis, the analyte ions having bypassed the ion trap.

5. The method of claim 4, wherein the analyte ions and reference ions are guided along an axis through the ion guide, and wherein an electric field is applied to the reference ions whilst they are within the ion guide or at the exit of the ion guide such that the reference ions are diverted off the axis and transmitted downstream into the ion trap and trapped therein; and/or wherein an electric field is applied to the analyte ions whilst they are within the ion guide or at the exit of the ion guide such that the analyte ions are diverted off the axis and transmitted downstream into the analyser whilst bypassing the ion trap.

6. The method of claim 4, wherein a second ion guide is provided between the first ion guide and the analyser for guiding ions to the analyser, wherein analyte ions are transmitted from the first ion guide into the second ion guide and then into the analyser whilst bypassing the ion trap, and wherein reference ions are transmitted from the ion trap into the second ion guide and into the analyser.

7. The method of claim 6, wherein the first and second ion guides have longitudinal axes along which ions travel as they pass through the ion guides, and wherein the longitudinal axes are coaxial and arranged such that ions which exit the first ion guide along its longitudinal axis are directed into the second ion guide.

8. The method of claim 4, wherein a mass analyser and/or ion mobility separator and/or ion filter is provided between the source of analyte ions and the first ion guide for mass analysing analyte ions, for separating analyte ions according to their mass to charge ratios or ion mobilities, or mass selectively transmitting analyte ions; and/or
wherein a mass analyser and/or ion mobility separator and/or ion filter is provided between the source of reference ions and the first ion guide for mass analysing reference ions, separating reference ions from other ions according to their mass to charge ratios or ion mobilities, or mass selectively transmitting reference ions.

9. The method of claim 1, wherein the analyte ions are generated by a first ion source and the reference ions are generated by a second, different ion source; wherein analyte ions are guided from the analyte ion source into the analyser by a first ion guide; and wherein reference ions are guided from the reference ion source into the ion trap by a second, different ion guide.

10. The method of claim 9, wherein reference ions are released from said ion trap into said first ion guide and are then guided into the analyser.

11. The method of claim 10, wherein the first ion guide comprises a switching device that operates in a first mode to allow analyte ions to pass from the analyte ion source into the analyser, and that operates in a second mode to prevent analyte ions from passing from the analyte ion source to the analyser and to allow reference ions to pass from the ion trap to the analyser.

12. The method of claim 1, comprising operating a first mode in which analyte ions are analysed in the analyser and reference ions are not, operating a second mode in which reference ions from the ion trap are analysed in the analyser and analyte ions are not, and wherein the method is repeatedly alternated between these first and second modes.

13. The method of claim 1, wherein the analyser discontinuously analyses ions in a plurality of analysis cycles and wherein reference ions are guided into the analyser as a series of ion packets that are synchronised with the analysis cycles such that an ion packet is analysed in at least one cycle or between cycles; and wherein spectral data from the reference ions analysed in separate analysis cycles is combined to produce combined reference ion data or a combined reference ion peak that is used to either:
  (i) adjust or calibrate the mass or mobility measurements of the analyte ions; or
  (ii) maintain a predetermined operational characteristic of the mass or ion mobility spectrometer at a desired level, e.g. to maintain the mass or ion mobility spectrometer at a desired resolution or sensitivity.

14. The method of claim 1, wherein the analyte ions do not pass into the ion trap and/or wherein the only ions that enter the ion trap are the reference ions.

15. The method of claim 1, wherein the reference ions are released from the ion trap into the analyser for calibrating the analyser for the analysis of the analyte ions that have bypassed the ion trap.

16. The method of claim 1, wherein the analyte ions are transmitted from the ion source of analyte ions to the analyser without being reacted with other ions or molecules, and/or without being fragmented.

17. The method of claim 1, wherein reference ions are released from the ion trap at a substantially constant charge per second.

18. The method of claim 1, wherein reference ions are discontinuously released from the ion trap in ion packets having substantially the same charge.

19. The method of claim 1, wherein the reference ions are released from the ion trap at a rate such that the reference ions do not saturate the analyser or a detector of said analyser.

20. A mass or ion mobility spectrometer comprising:
an ion source for generating analyte ions and an ion source for generating reference ions;
an analyser;
an ion trap arranged between the ion source for generating reference ions and the analyser; and
control means arranged and configured to:
direct reference ions from the ion source for generating reference ions into the ion trap and trap the reference ions therein;
direct analyte ions from the ion source for generating analyte ions into the analyser without the analyte ions passing into the ion trap, and to analyse the analyte ions in the analyser; and
release the reference ions from the ion trap into the analyser so as to analyse the reference ions, wherein the trapped reference ions are controllably released from the ion trap such that only a portion of the reference ions trapped in the ion trap are released at any given time.

21. A method of mass or ion mobility spectrometry comprising:
- providing an ion source for generating analyte ions and an ion source for generating reference ions;
- providing an analyser;
- providing an ion trap between the ion source for generating reference ions and the analyser;
- directing reference ions from the ion source for generating reference ions into the ion trap and trapping the reference ions therein;
- directing analyte ions from the ion source for generating analyte ions into the analyser without the analyte ions passing into the ion trap, and analysing the analyte ions in the analyser; and
- releasing reference ions from the ion trap into the analyser and analysing the reference ions.

22. The method of claim 21, wherein reference ions and analyte ions are guided through the same first ion guide, wherein the reference ions are directed from the ion guide into the trap and trapped therein, and wherein the analyte ions are directed from the ion guide into the analyser for analysis, the analyte ions having bypassed the ion trap.

* * * * *